United States Patent
Chen et al.

(10) Patent No.: US 9,957,240 B2
(45) Date of Patent: May 1, 2018

(54) CRYSTALLINE FORMS OF TRISODIUM SUPRAMOLECULAR COMPLEX COMPRISING VALSARTAN AND AHU-377 AND METHODS THEREOF

(71) Applicants: CRYSTAL PHARMATECH CO., LTD, Suzhou, Jiangsu (CN); SUZHOU PENGXU PHARMATECH CO., LTD., Suzhou (CN)

(72) Inventors: Minhua Chen, Scotch Plains, NJ (US); Yanfeng Zhang, Suzhou (CN); Chaohui Yang, Suzhou (CN); Xiaoyu Zhang, Suzhou (CN); Jiaoyang Li, Suzhou (CN); Peng Wang, New York, NY (US); Pixu Li, Suzhou (CN)

(73) Assignees: CRYSTAL PHARMATECH CO., LTD, Suzhou, Jiangsu (CN); SUZHOU PENGXU PHARMATECH CO., LTD., Suzhou (CN)

( * ) Notice: Subject to any disclaimer, the term of this patent is extended or adjusted under 35 U.S.C. 154(b) by 0 days. days.

(21) Appl. No.: 15/528,153

(22) PCT Filed: Dec. 8, 2015

(86) PCT No.: PCT/US2015/064432
§ 371 (c)(1),
(2) Date: May 19, 2017

(87) PCT Pub. No.: WO2016/049663
PCT Pub. Date: Mar. 31, 2016

(65) Prior Publication Data
US 2017/0362189 A1 Dec. 21, 2017

Related U.S. Application Data

(60) Provisional application No. 62/089,225, filed on Dec. 8, 2014.

(51) Int. Cl.
*C07D 257/04* (2006.01)

(52) U.S. Cl.
CPC ........ *C07D 257/04* (2013.01); *C07B 2200/13* (2013.01)

(58) Field of Classification Search
CPC .................................................... C07D 257/04
See application file for complete search history.

*Primary Examiner* — Paul V Ward
(74) *Attorney, Agent, or Firm* — VLP Law Group, LLP

(57) ABSTRACT

Novel crystalline Forms of trisodium [3-((1S,3R)-1-biphenyl-4-ylmethyl-3-ethoxycarbonyl-1-butyl carbamoyl) propionate-(S)-3'-methyl-T-(pentanoyl{2"-(tetrazol-5-ylate)biphenyl-4'-ylmethyl}amino)butyrate] hydrate, methods for their preparation, pharmaceutical compositions comprising these new forms, and use of them for treating or delaying progression or onset of diseases or disorders related to activity of angiotensin receptor 1 (AT1) blockage and neprilysin (NEP) inhibition, such as heart failure, are disclosed.

19 Claims, 10 Drawing Sheets

CRYSTALLINE FORMS OF TRISODIUM SUPRAMOLECULAR COMPLEX COMPRISING VALSARTAN AND AHU-377 AND METHODS THEREOF

CROSS REFERENCE TO RELATED APPLICATIONS

This application claims priority under 35 U.S.C. § 119(e) to Provisional Application No. 62/089,225, filed on Dec. 8, 2014, which is herein incorporated by reference in its entirety.

FIELD OF THE INVENTION

This invention relates to novel crystalline forms of trisodium supramolecular complexes comprising valsartan and AHU-377, and pharmaceutical compositions, methods of preparation, and methods of uses thereof.

BACKGROUND OF THE INVENTION

Heart failure (HF) is a major and increasing clinical problem that is associated with substantial morbidity and mortality. It is the leading cause of admission to hospital in individuals older than 65 years.

As the population lives longer resulting in an increased prevalence of cardiovascular risk factors and diseases, and as survival following acute myocardial infarction (MI) increases, the number of patients living with congestive heart failure (CHF) is expanding. For example, risk factors such as hypertension are common prognostic comorbidities in chronic HF. In parallel, a concomitant increase in the number of hospitalizations for acute decompensated heart failure (ADHF) has occurred. In the United States alone, heart failure (HF) affects 5.7 million Americans, with over 650,000 new cases diagnosed annually, with increasing hospitalization rates.

Heart failure remains a high unmet medical need with an annual mortality rate of about 20%. Reductions in mortality and cardiovascular morbidity have been achieved by the renin-angiotensin-aldosterone system (RAAS) blockers (Angiotensin Converting Enzyme (ACE) inhibitors and Angiotensin Receptor Blockers (ARBs)) and beta (3)-blockers in HF. While survival rates have improved for HF with reduced ejection fraction (HF-REF) over recent decades, due to more widespread use of drugs that block RAAS and improved acute care, residual mortality rates remain high. For patients with HF with preserved ejection fraction (HF-PEF) no therapy has proven to be effective at reducing morbidity and mortality. Overall, the therapeutic benefits of RAAS blockade with ACE inhibitors and/or ARBs remain limited, possibly caused by angiotensin II escape due to incomplete ACE inhibition or angiotensin II originating from alternative non-ACE pathways, and by other neurohormonal and other mechanisms contributing to cardiac disease and outcomes.

A supramolecular complex comprising valsartan, which is an ARB, and AHU-377 (Sacubitril), which is a neprilysin inhibitor, has been approved by US Food and Drug Administration (FDA) under the brand name Entresto for the treatment of heart failure with reduced ejection fraction.

Valsartan blocks the angiotensin II receptor type 1 (AT1). This receptor is found on both vascular smooth muscle cells and the zona glomerulosa cells of the adrenal gland which are responsible for aldosterone secretion. In the absence of AT1 blockade, angiotensin causes both direct vasoconstriction and adrenal aldosterone secretion, the aldosterone then acting on the distal tubular cells of the kidney to promote sodium reabsorption which expands extracellular fluid (ECF) volume. Blockade of (AT1) thus causes vasodilation and reduction of ECF volume.

AHU-377 is a prodrug that is activated to sacubitrilat (LBQ657) by de-ethylation via esterases. AHU-377 inhibits the enzyme neprilysin, a neutral endopeptidase that degrades vasoactive peptides, including natriuretic peptides, bradykinin, and adrenomedullin. Thus, AHU-377 increases the levels of these peptides, causing vasodilation and reduction of ECF volume via sodium excretion.

Entresto is a first-in-class medicine (an Angiotensin Receptor Neprilysin Inhibitor, or ARNI) and has a unique mode of action which is thought to reduce the strain on the failing heart. It harnesses the body's natural defenses against heart failure, simultaneously acting to enhance the levels of natriuretic and other endogenous vasoactive peptides, while also inhibiting the renin-angiotensin-aldosterone system (RAAS).

Furthermore, crystallinity of drugs effects, among other physical and mechanical properties, their solubility, dissolution rate, hardness, compressability and melting point. Because these properties may, in turn, effect a drug's manufacture and their utility, there is an existing need in the chemical and therapeutic arts for identification of crystalline forms of drugs and ways of reproducibly making them.

Though one crystalline form of the supramolecular complex comprising valsartan and AHU-377 has been reported to exist as a trisodium hemipentahydrate form in U.S. Pat. No. 8,877,938 B2 (the "patent form"), new crystalline forms of the supramolecular complex comprising valsartan and AHU-377, in particular stable polymorphs with superior pharmacological activities suitable for formulation, and convenient methods to prepare them remain a great need.

SUMMARY OF THE INVENTION

The present invention provides crystalline forms of supramolecular complex comprising valsartan and AHU-377 and having desired physicochemical properties, for example, less hygroscopic and/or better flowability, which make them more suitable for use in dosage forms to achieve desired bioavailability and therapeutic effects. The crystalline forms disclosed herein can also be prepared conveniently at a low cost.

The supramolecular complexes of this invention are trisodium [3-((1S,3R)-1-biphenyl-4-ylmethyl-3-ethoxycarbonyl-1-butylcarbamoyl) propionate-(S)-3'-methyl-2'-(pentanoyl{2''-(tetrazol-5-ylate) biphenyl-4'-ylmethyl}amino) butyrate] hydrates, having a structure of general Formula I:

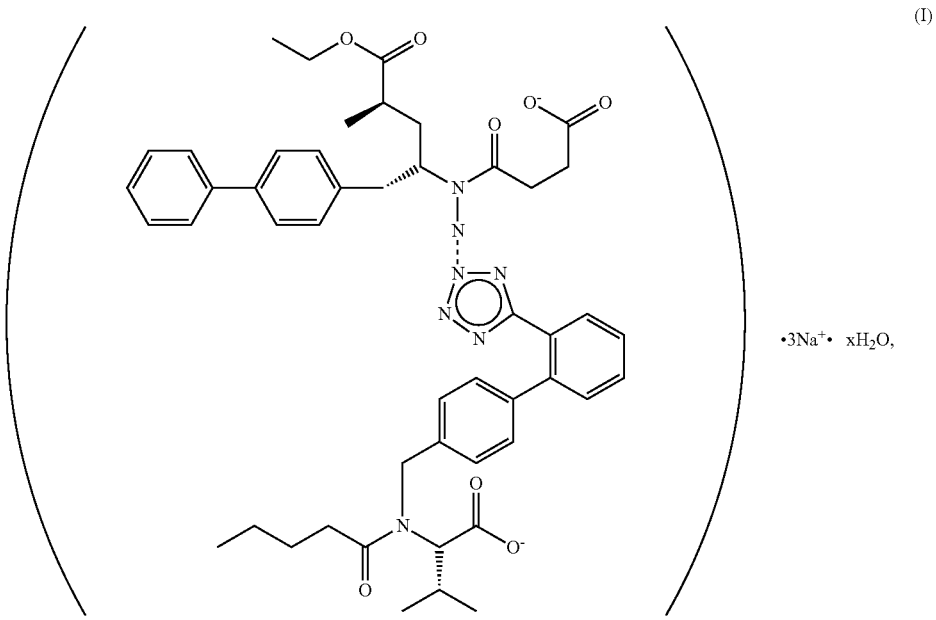

wherein x is a number in the range of 0.5-4.0.

In one aspect, the present invention provides a crystalline form of trisodium [3-((1S, 3R)-1-biphenyl-4-ylmethyl-3-ethoxycarbonyl-1-butylcarbamoyl) propionate-(S)-3'-methyl-2'-(pentanoyl{2"-(tetrazol-5-ylate) biphenyl-4'-ylmethyl}amino) butyrate] hydrate designated as Form I.

In another aspect, the present invention provides a crystalline form of trisodium [3-((1 S, 3R)-1-biphenyl-4-ylmethyl-3-ethoxycarbonyl-1-butylcarbamoyl) propionate-(S)-3'-methyl-2'-(pentanoyl{2"-(tetrazol-5-ylate) biphenyl-4'-ylmethyl}amino) butyrate] hydrate designated as Form II.

In another aspect, the present invention provides a crystalline form of trisodium [3-((1 S, 3R)-1-biphenyl-4-ylmethyl-3-ethoxycarbonyl-1-butylcarbamoyl) propionate-(S)-3'-methyl-2'-(pentanoyl{2"-(tetrazol-5-ylate) biphenyl-4'-ylmethyl}amino) butyrate] hydrate designated as Form III.

In another aspect, the present invention provides processes for preparation of crystalline Form I.

In another aspect, the present invention provides processes for preparation of crystalline Form II.

In another aspect, the present invention provides processes for preparation of crystalline Form III.

In other aspects, the present invention provides pharmaceutical compositions comprising a supramolecular complex of valsartan and AHU-377 selected from the group consisting of crystalline Form I, Form II, Form III, and combinations thereof, and a pharmaceutically acceptable carrier.

In another aspect, the present invention is directed to methods for treatment of a patient suffering from a disease or condition selected from hypertension, heart failure, congestive heart failure, left ventricular dysfunction and hypertrophic cardiomyopathy, diabetic cardiac myopathy, supraventricular and ventricular arrhythmias, atrial fibrillation, atrial flutter, detrimental vascular remodeling, myocardial infarction, atherosclerosis, angina, renal insufficiency, angina pectoris, diabetes, secondary aldosteronism, primary and secondary pulmonary hypertension, and renal failure conditions, the method comprising administering to the patient a therapeutically effective amount of a supramolecular complex of valsartan and AHU-377 selected from the group consisting of crystalline Form I, Form II, Form III, and combinations thereof, or a pharmaceutical composition comprising any of the crystalline Forms or combinations thereof.

In another aspect, the present invention is directed to the use of any of the crystalline Form I, Form II, and Form III of the valsartan and AHU-377 supramolecular complexes, or combinations thereof, or a composition comprising any of the crystalline Form I, Form II, and Form III, or combinations thereof, in the manufacture of a medicament for treating or delaying progression or onset of a disease or disorder related to activity of angiotensin receptor 1 (AT1) and neprilysin (NEP).

Other aspects and embodiments of the present invention will be further illustrated in the following description and examples.

DETAILED DESCRIPTION OF THE INVENTION

The present invention is based on a surprising discovery that a supramolecular complex comprising valsartan and AHU-377 could exist in various new crystalline Forms having superior physicochemical properties as compared to the patent form.

In one aspect, the present invention provides the supramolecular complex of tri sodium [3-((1S,3R)-1-biphenyl-4-ylmethyl-3-ethoxycarbonyl-1-butylcarbamoyl) propionate-(S)-3'-methyl-2'-(pentanoyl{2"-(tetrazol-5-ylate) biphenyl-4'-ylmethyl}amino) butyrate] hydrate in crystalline Form I.

In one embodiment, the crystalline Form I is characterized by an X-ray powder diffraction pattern comprising the following 2θ values measured using CuKα radiation: 5.1°±0.2°, 4.1°±0.2°, and 19.8°±0.2°.

In another embodiment, crystalline Form I is characterized by an X-ray powder diffraction pattern further comprising the following 2θ values measured using CuKα radiation: 12.5°±0.2°, and 16.9°±0.2°.

In another embodiment, crystalline Form I is characterized by an X-ray powder diffraction pattern further comprising the following 2θ values measured using CuKα radiation: 14.9°±0.2°, 17.7°±0.2°, and 18.0°±0.2°.

In another embodiment, crystalline Form I is characterized by an X-ray powder diffraction pattern comprising the following 2θ values measured using CuKα radiation: 4.1°±0.2°, 5.1°±0.2°, 12.5°±0.2°, 14.9°±0.2°, 16.9°±0.2°, 17.7°±0.2°, 18.0°±0.2°, and 19.8°±0.2°.

Figure 1:
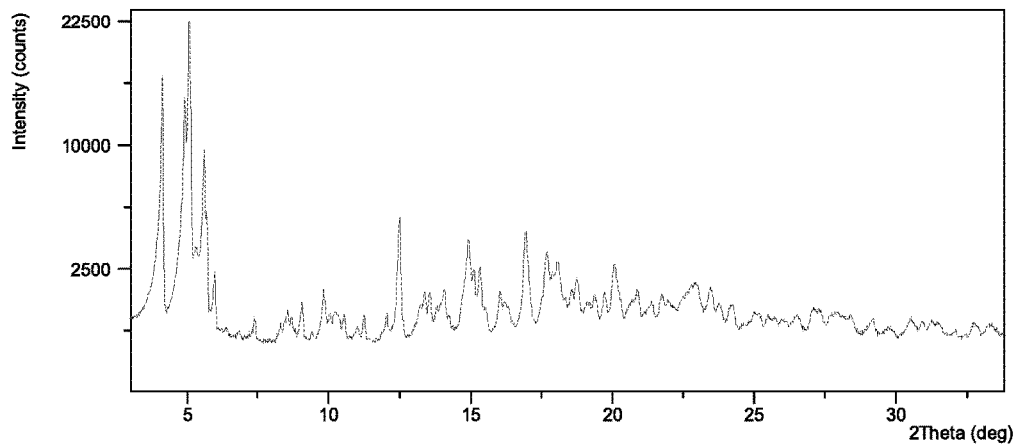
FIG. 1 shows an X-ray powder diffraction (XRPD) pattern of crystalline Form I obtained from example 1

In another embodiment, crystalline Form I has an X-ray powder diffraction pattern substantially as shown in FIG. 1.

In another embodiment, crystalline Form I has a differential scanning calorimetry thermogram which exhibits two endothermic peaks with onset temperatures of about 70° C.-100° C. and about 125° C.-130° C., respectively.

Figure 3:
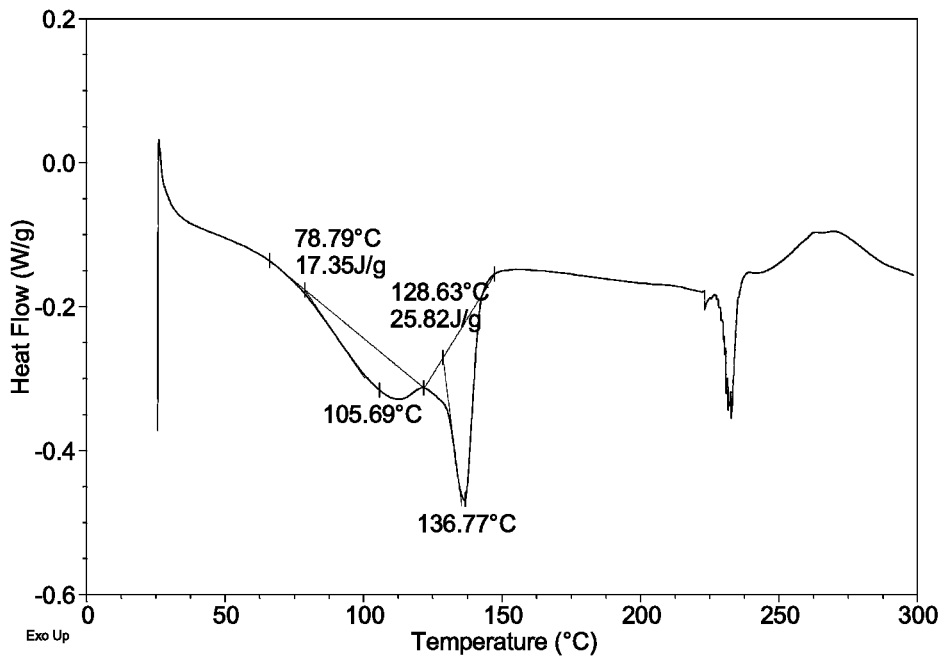
FIG. 3 shows a differential scanning calorimetry (DSC) thermogram of crystalline Form I obtained from example 2

In a preferred embodiment, crystalline Form I has a differential scanning calorimetry thermogram substantially as shown in FIG. 3, which exhibits two endothermic peaks with onset temperatures of about 78.8° C. and about 128.6° C.

While not intended to be limiting, crystalline Form I may be a hydrate with each molecule containing 2.5 to 4.0 molecules of $H_2O$ (x equals 2.5 to 4.0 in formula I). More preferred, crystalline Form I may be a hydrate with each molecule containing 3.0 to 4.0 molecules of $H_2O$ (x equals 3.0 to 4.0 in formula I).

In another aspect, the present invention provides a process for preparation of the supramolecular complex crystalline Form I, selected from the processes described below:

1) dissolving valsartan, AHU-377 and sodium hydroxide in one or more alkyl ketones to form a solution; stirring the mixture at room temperature until crystalline Form I precipitates out; or 2) stirring crystalline Form II (see below) in one or more aromatic hydrocarbons in a temperature range of about 40° C. to 80° C., preferably about 50° C.

In some embodiments, said alkyl ketones are selected from acetone, methyl ethyl ketone, methyl isobutyl ketone, and the like, and preferably acetone.

In some embodiments, said aromatic hydrocarbons are selected from toluene, ethylbenzene, cumene, and the like, and preferably cumene.

In some embodiments, the molar ratio of valsartan to AHU-377 is in the range of 1.2 to 0.8.

In some embodiments, the molar ratio of sodium hydroxide to valsartan is in the range of 2.0 to 4.0, preferably about 3.0.

In another aspect, the present invention provides the supramolecular complex of tri sodium [3-((1S,3R)-1-biphenyl-4-ylmethyl-3-ethoxycarbonyl-1-butylcarbamoyl) propionate-(S)-3'-methyl-2"-(pentanoyl{2"-(tetrazol-5-ylate) biphenyl-4'-ylmethyl}amino) butyrate] hydrate in crystalline Form II.

In one embodiment, crystalline Form II is characterized by an X-ray powder diffraction pattern comprising the following 2θ values measured using CuKα radiation: 4.3°±0.2°, 5.0°±0.2°, and 12.8°±0.2°.

In another embodiment, crystalline Form II is characterized by an X-ray powder diffraction pattern further comprising the following 2θ values measured using CuKα radiation: 5.5°±0.2°, 5.8°±0.2°, and 18.9°±0.2°.

In another embodiment, crystalline Form II is characterized by an X-ray powder diffraction pattern further comprising the following 2θ values measured using CuKα radiation: 14.6°±0.2°, 18.5°±0.2°, and 20.1°±0.2°.

In another embodiment, crystalline Form II is characterized by an X-ray powder diffraction pattern comprising the following 2θ values measured using CuKα radiation: 4.3°±0.2°, 5.0°±0.2°, 5.5°±0.2°, 5.8°±0.2°, 12.8°±0.2°, 14.6°±0.2°, 18.5°±0.2°, 18.9°±0.2°, and 20.1°±0.2°.

Figure 7:
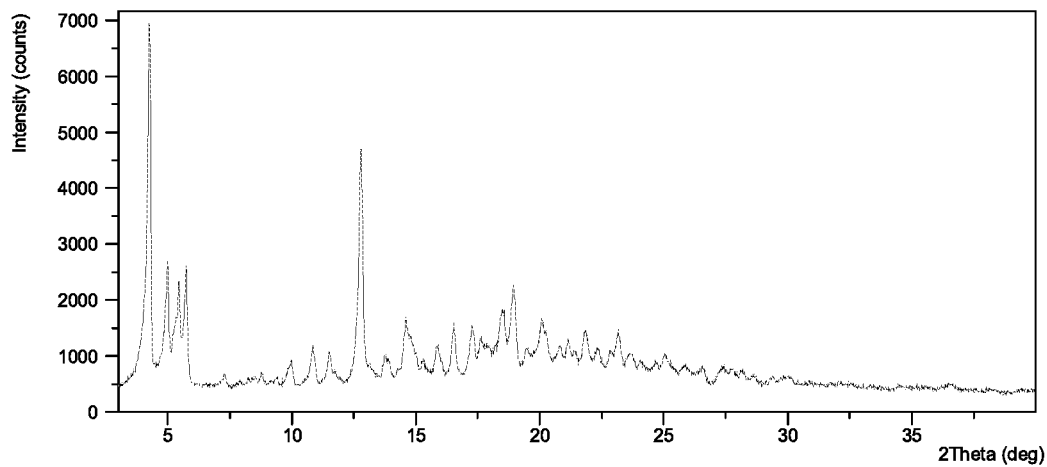
FIG. 7 shows an X-ray powder diffraction (XRPD) pattern of crystalline Form II obtained from example 6

In another embodiment, crystalline Form II has an X-ray powder diffraction pattern substantially as shown in FIG. 7.

In another embodiment, crystalline Form II has a differential scanning calorimetry thermogram which exhibits two endothermic peaks with onset temperatures of about 70° C.-100° C. and about 110° C.-130° C., respectively.

Figure 9:
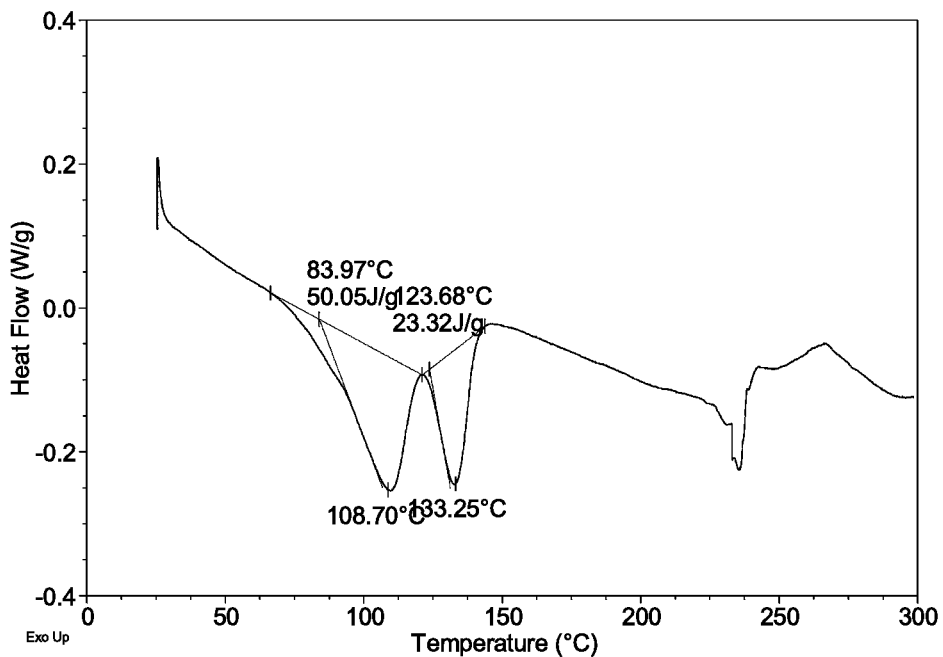
FIG. 9 shows a differential scanning calorimetry (DSC) thermogram of crystalline Form II obtained from example 7

In a preferred embodiment, crystalline Form II has a differential scanning calorimetry thermogram substantially as shown in FIG. 9, which exhibits two endothermic peaks with onset temperatures of about 84.0° C. and about 123.7° C.

While not intended to be limiting, crystalline Form II may be a hydrate with each molecule containing 2.5 to 4.0 molecules of $H_2O$ (x equals 2.5 to 4.0 in formula I). More preferred, crystalline Form II may be a hydrate with each molecule containing 3.0 to 4.0 molecules of $H_2O$ (x equals 3.0 to 4.0 in formula I).

In another aspect, the present invention provides a process for preparation of the supramolecular complex crystalline Form II, selected from the processes described below:

1) dissolving trisodium [3-((1S,3R)-1-biphenyl-4-ylmethyl-3-ethoxycarbonyl-1-butylcarbamoyl) propionate-(S)-3'-methyl-2'-(pentanoyl{2"-(tetrazol-5-ylate)biphenyl-4'- ylmethyl}amino)butyrate] hemipentahydrate in one or more alcohols to form a solution, adding one or more aromatic hydrocarbons to the solution, and stirring the mixture at room temperature until solids (Form II) precipitate out; or 2) dissolving trisodium [3-((1S,3R)-1-biphenyl-4-ylmethyl-3-ethoxycarbonyl-1-butylcarbamoyl) propionate-(S)-3'-methyl-2'-(pentanoyl{2"-(tetrazol-5-ylate) biphenyl-4'-ylmethyl}amino) butyrate] hemipentahydrate in one or two solvents selected from the group consisting of alcohols and aromatic hydrocarbons to form a solution; and evaporating the solvent(s) at room temperature until solids (Form II) precipitate out.

In some embodiments, said alcohols are selected from the group consisting of methanol, ethanol, propanol, butanol, and the like, and preferably methanol.

In some embodiments, said aromatic hydrocarbons are selected from the group consisting of toluene, ethylbenzene, cumene, and the like, and preferably toluene.

In another aspect, the present invention provides the supramolecular complex of trisodium [3-((1S,3R)-1-biphenyl-4-ylmethyl-3-ethoxycarbonyl-1-butylcarbamoyl) propionate-(S)-3'-methyl-2'-(pentanoyl{2"-(tetrazol-5-ylate) biphenyl-4'-ylmethyl}amino) butyrate] hemihydrate in crystalline Form III.

In one embodiment, crystalline Form III is characterized by an X-ray powder diffraction pattern comprising the following 2θ values measured using CuKα radiation: 17.2°±0.2°, 18.4°±0.2°, and 18.7°±0.2°.

In another embodiment, crystalline Form III is characterized by an X-ray powder diffraction pattern further comprising the following 2θ values measured using CuKα radiation: 4.1°±0.2°, 12.4°±0.2°, and 15.3°±0.2°.

In another embodiment, crystalline Form III is characterized by an X-ray powder diffraction pattern further comprising the following 2θ values measured using CuKα radiation: 19.6°±0.2°, 25.0°±0.2°, 8.2°±0.2° and 16.5°±0.2°.

In another embodiment, crystalline Form III is characterized by an X-ray powder diffraction pattern comprising the following 2θ values measured using CuKα radiation: 4.1°±0.2°, 8.2°±0.2°, 12.4°±0.2°, 15.3°±0.2°, 16.5°±0.2°, 17.2°±0.2°, 18.4°±0.2°, 18.7°±0.2°, 19.6°±0.2°, and 25.0°±0.2°.

Figure 15:
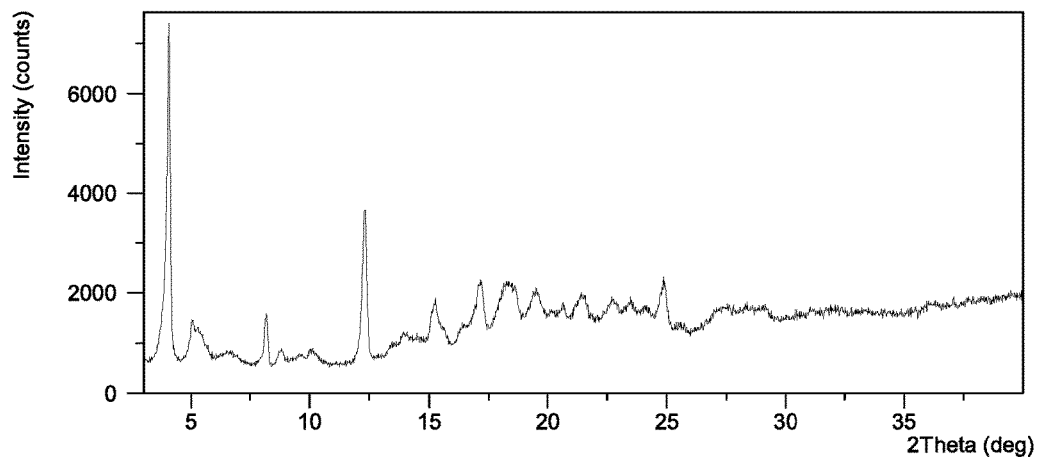
FIG. 15 shows an X-ray powder diffraction (XRPD) pattern of crystalline Form III obtained from example 12

In another embodiment, crystalline Form III has an X-ray powder diffraction pattern substantially as shown in FIG. 15.

In another embodiment, crystalline Form III has a differential scanning calorimetry thermogram which exhibits an endothermic peak with an onset temperature of about 130° C.-140° C.

Figure 16:
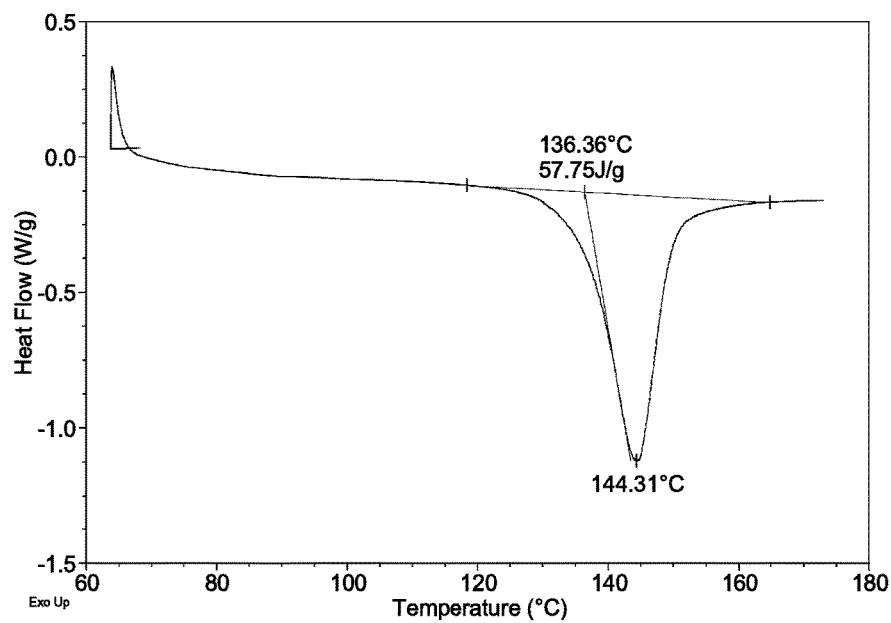
FIG. 16 shows a differential scanning calorimetry (DSC) thermogram of crystalline Form III obtained from example 12

In a preferred embodiment, crystalline Form III has a differential scanning calorimetry thermogram substantially as shown in FIG. 16, which exhibits an endothermic peak with an onset temperature of about 136.4° C.

While not intended to be limiting, Form III may be a hydrate with each molecule containing 0.5 to 2 molecules of $H_2O$ (x equals 0.5 to 2.0 in formula I). More preferred, crystalline Form III may be a hydrate with each molecule containing 0.5 molecules of $H_2O$ (x equals 0.5 in formula I). In another aspect, the present invention provides a process for preparation of the supramolecular complex crystalline Form III, which comprises the step of heating Form I to a temperature in the range of about 100° C. to about 140° C., preferably about 120° C.

In another aspect, the present invention provides pharmaceutical compositions comprising a therapeutically effective amount of a supramolecular complex trisodium [3-((1S,3R)-1-biphenyl-4-ylmethyl-3-ethoxycarbonyl-1-butylcarbamoyl) propionate-(S)-3'-methyl-2'-(pentanoyl{2"-(tetrazol-5-ylate)biphenyl-4'-ylmethyl}amino) butyrate] hydrate in any of crystalline Form I, Form II, and Form III, or combinations thereof, and a pharmaceutically acceptable carrier.

Crystalline Forms I, II, and III of the supramolecular complex comprising valsartan and AHU-377, together with one or more pharmaceutically acceptable excipients, of the present invention may be further formulated as: solid oral dosage forms such as, but not limited to, powders, granules, pellets, tablets, and capsules; liquid oral dosage forms such as, but not limited to, syrups, suspensions, dispersions, and emulsions; and injectable preparations such as, but not limited to, solutions, dispersions, and freeze dried compositions. Formulations may be in the forms of immediate release, delayed release or modified release. Further, immediate release compositions may be conventional, dispersible, chewable, mouth dissolving, or flash melt preparations; and modified release compositions may comprise hydrophilic or hydrophobic, or combinations of hydrophilic and hydrophobic, release rate controlling substances to form matrix or reservoir, or combination of matrix and reservoir systems. The compositions may be prepared using techniques such as direct blending, dry granulation, wet granulation, and extrusion and spheronization. Compositions may be presented as uncoated, film coated, sugarcoated, powder coated, enteric coated, or modified release coated.

In another aspect, the present invention provides pharmaceutical compositions comprising any one of the crystalline Form I, Form II, and Form III, or combinations thereof, and a pharmaceutically acceptable carrier.

In another aspect, the present invention is directed to a method of treating a patient suffering from hypertension, heart failure, congestive heart failure, left ventricular dysfunction and hypertrophic cardiomyopathy, diabetic cardiac myopathy, supraventricular and ventricular arrhythmias, atrial fibrillation, atrial flutter, detrimental vascular remodeling, myocardial infarction, atherosclerosis, angina, renal insufficiency, angina pectoris, diabetes, secondary aldosteronism, primary and secondary pulmonary hypertension, and/or renal failure conditions, the method comprising administering to the patient a therapeutically effective amount of a supramolecular complex of valsartan and AHU-377 selected from the group consisting of crystalline Form I, Form II, Form III, and combinations thereof, or a pharmaceutical composition comprising any of the crystalline Forms or combinations thereof.

In another aspect, the present invention is directed to the use of any of the supramolecular complex Form I, Form II, and Form III, or combinations thereof in the manufacture of a medicament for treating or delaying progression or onset of a disease or disorder related to activity of angiotensin receptor 1 (AT1) and neprilysin (NEP).

Disease or disorder related to activity of angiotensin receptor 1 (AT1) and neprilysin (NEP) include, but are not limited to heart failure, cardiac dysrhythmias; mitral stenosis and regurgitation, cardiomyopathies, hypertension and pulmonary heart diseases. In one embodiment, cardiac dysrhythmias comprise atrial fibrillation, new onset atrial fibrillation and recurrent atrial fibrillation. In one embodiment, heart failure comprises congestive heart failure, left heart failure, right heart failure, chronic heart failure, advanced heart failure, acute heart failure, acute decompensated heart failure, heart failure with reduced ejection fraction (HF-REF), and heart failure with preserved ejection fraction (HF-PEF). In particular, heart failure comprises heart failure with preserved ejection fraction (HF-PEF) and heart failure with reduced ejection fraction (HF-REF).

In one embodiment, the mammal suffers from hypertension or heart failure or is prone to suffering from hypertension and/or heart failure. In one embodiment said patients suffering from heart failure are patients suffering from heart failure with preserved ejection fraction (HF-PEF) or heart failure with reduced ejection fraction (HF-REF). In one embodiment said patients suffering from heart failure are patients suffering from heart failure with preserved ejection fraction (HF-PEF).

In another embodiment, the mammal suffers from hypertension.

In another embodiment, the mammal has an enlarged heart.

In another embodiment, the mammal has atherosclerosis.

In another aspect, the present invention is directed to a pharmaceutical solid formulation comprising a unit dosage of crystalline Form I, crystalline Form II or crystalline Form III of tri sodium [3-((1S,3R)-1-biphenyl-4-ylmethyl-3-ethoxycarbonyl-1-butylcarbamoyl) propionate-(S)-3'-methyl-2'-(pentanoyl{2''-(tetrazol-5-ylate) biphenyl-4'-ylmethyl}amino) butyrate] hydrate and one or more excipients selected from the group consisting of fillers, disintegrants, glidants, and lubricants.

In one embodiment, said filler is microcrystalline cellulose and/or hydroxypropyl cellulose; said disintegrant is crospovidone; said glidant is colloidal silicon dioxide; and said lubricant is talc or magnesium stearate.

In another embodiment, the pharmaceutical solid formulation is a tablet or capsule.

In another embodiment, the pharmaceutical solid formulation for treatment of a disease or disorder selected from the group consisting of hypertension, heart failure, congestive heart failure, left ventricular dysfunction and hypertrophic cardiomyopathy, diabetic cardiac myopathy, supraventricular and ventricular arrhythmias, atrial fibrillation, atrial flutter, detrimental vascular remodeling, myocardial infarction, atherosclerosis, angina, renal insufficiency, angina pectoris, diabetes, secondary aldosteronism, primary and secondary pulmonary hypertension, and renal failure conditions.

The crystalline Forms I, II, and III of the present invention may include the improvements/advantages over the existing crystalline Forms disclosed in U.S. Pat. No. 8,877,938B2 (the "patent form"), such as superior physicochemical properties, which can facilitate formulation and manufacture processes and enhance absorption and/or bioavailability.

In particular, Form I is less hygroscopic when exposed to humidity levels ranging from 20% RH to 60% RH at 25° C. compared to patent form; Form II is less hygroscopic when exposed to humidity levels ranging from 50% RH to 60% RH at 25° C. compared to patent form; and Form II exhibits better flowability than the patent form.

Definitions

Throughout this specification and in the claims that follow, the following terms are defined with the following meanings, unless explicitly stated otherwise.

The terms in the present invention, if not specifically defined, take their ordinary meanings as would be understood by those skilled in the art.

The term "alcohol," "alcoholic solvent," or the like, refers to $C_1$-$C_6$ alkyl alcohol, preferably $C_1$-$C_4$ alkyl alcohol, for example, in some embodiments preferably, methanol, ethanol, isopropanol, or the like.

The term "ketone," "alkyl ketone," or the like, refers to $C_3$-$C_7$ alkanone, having a formula RCOR', wherein R and R' are each independently $C_1$-$C_4$ alkyl, for example, in some embodiments preferably, acetone, butanone, 2-pentanone, 3-pentanone, methyl isobutyl ketone (MIBK), or the like.

The term "aromatic hydrocarbon," or the like, refers to benzene optionally substituted by 1 to 3 methyl or ethyl groups, for example, in some embodiments preferably, toluene, 1,2-xylene, 1,4-xylene, 1,3-xylene, cumene, ethylbenzene, or the like.

The term "supramolecular complex" is intended to describe an interaction between the two pharmaceutically active agents, the cations and any other entity present such as a solvent, in particular water, by means of noncovalent, intermolecular bonding between them. This interaction leads to an association of the species present in the supramolecular complex distinguishing this complex over a physical mixture of the species. The supramolecular complex shows properties such as melting point, IR spectrum, etc. that are different from a physical mixture of the species.

The term "treatment" refers to the management and care of a patient for the purpose of combating the disease, condition or disorder.

The term "therapeutically effective amount" refers to an amount of a drug or a therapeutic agent that will elicit the desired biological and/or medical response of a tissue, system or an animal (including man) that is being sought by a researcher or clinician.

The term "mammal" include, but are not limited to, humans, dogs, cats, horses, pigs, cows, monkeys, rabbits and mice. The preferred mammals are humans.

The term "administering" means applying a compound of the invention, or a pharmaceutically acceptable salt, prodrug or composition thereof, to a subject in need of treatment. The administration of the composition of the present invention in order to practice the present methods of therapy is carried out by administering a therapeutically effective amount of the compounds in the composition to a subject in need of such treatment or prophylaxis. The need for a prophylactic administration according to the methods of the present invention is determined via the use of well-known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration, other drugs and treatments which the patient may concomitantly require, and other factors in the physician's judgment.

The term "pharmaceutically acceptable", as used herein, refers to those compounds, materials, compositions and/or dosage forms, which are, within the scope of sound medical judgment, suitable for contact with the tissues of mammals, especially humans, without excessive toxicity, irritation, allergic response and other problem complications commensurate with a reasonable benefit/risk ratio.

When the term "about" is applied to a parameter, such as amount, temperature, time, or the like, it indicates that the parameter can usually vary by ±10%, preferably within ±5%, and more preferably within ±2%. However, in the case of a melting or onset temperature of a crystalline form as measured by in a DSC thermogram, the term "about" may indicate that the melting or onset temperature can usually vary within ±2° C., regardless of the absolute value of the melting or onset temperature, as a person skilled in the art would understand it. As would be understood by a person skilled in the art, when a parameter is not critical, a number is often given only for illustration purpose, instead of being limiting.

The term "a," "an," or "the," as used herein, represents both singular and plural forms. In general, when either a singular or a plural form of a noun is used, it denotes both singular and plural forms of the noun.

The following non-limiting examples further illustrate certain aspects of the present invention.

EXAMPLES

X-ray Powder Diffraction (XRPD)

XRPD was performed with Panalytical Empyrean XRPD on a Si single crystal holder. The 2θ position was calibrated against Panalytical 640 Si powder standard. Details of XRPD method used in the experiments are listed below.

| Parameters | Settings/Values (Reflection Mode) |
|---|---|
| X-Ray wavelength | Cu, kα, |
|  | Kα1 (Å): 1.540598, Kα2 (Å): 1.544426 |
|  | Kα2/Kα1 intensity ratio: 0.50 |
| X-Ray tube setting | 45 kV, 40 mA |
| Divergence slit | Automatic |
| Scan mode | Continuous |

Persons skilled in the art of X-ray powder diffraction will realize that the relative intensity of peaks can be affected by, for example, grains above 30 microns in size and non-unitary aspect ratios that may affect analysis of samples. The skilled person will also realize that the position of reflections can be affected by the precise height at which the sample sits in the diffractometer and the zero calibration of the diffractometer. The surface planarity of the sample may also have a small effect.

When an XRPD pattern of a crystal form is described as comprising certain "representative" or "characteristic" peaks or 2θ values, they refer to more prominent peaks, or a subset thereof, in the XRPD pattern. Typically, "characteristic peaks" are defined as a subset of representative (prominent) peaks used to differentiate one crystalline polymorph or form from another crystalline polymorph or form. Characteristic peaks may be determined by evaluating which representative peaks, if any, are present in one crystalline polymorph of a compound but not in all other known crystalline polymorphs of that compound. However, not all crystalline polymorphs of a compound would necessarily have at least one characteristic peak. As a person of ordinary skill in the art would understand, in certain situations, the overall diffraction pattern should be used to determine whether a crystal form exists as described or claimed.

Differential Scanning Calorimetry (DSC)
  Analytical Instrument: TA Instruments Q2000 DSC.
  Heating rate: 5° C. per minute.
  Purge gas: nitrogen Thermal Gravimetric Analysis (TGA)
  Analytical Instrument: TA Instruments Q5000 TGA.
  Heating rate: 10° C. per minute.
  Purge gas: nitrogen.

Example 1

Preparation of Supramolecular Complex Comprising Valsartan and AHU-377 Crystalline Form I To 0.2 mL of cumene was suspended about 10 mg of Form II (see Example 6). Stirred it at 50° C. for about 6 days. The solid was isolated and Form I was obtained, which was analyzed by XRPD. The XRPD data obtained in this example is listed in Table 1. The XRPD pattern of the complex obtained from this example is displayed in FIG. 1.

TABLE 1

| Pos. [°2Th.] | d-spacing [Å] | Rel. Int. [%] |
|---|---|---|
| 5.1 | 17.5 | 100.0 |
| 4.1 | 21.6 | 71.1 |
| 4.9 | 18.1 | 61.6 |
| 5.6 | 15.9 | 40.7 |
| 12.5 | 7.1 | 20.6 |
| 5.7 | 15.6 | 20.3 |
| 16.9 | 5.2 | 17.0 |
| 14.9 | 5.9 | 15.5 |
| 5.3 | 16.8 | 13.5 |
| 17.7 | 5.0 | 12.7 |
| 18.1 | 4.9 | 10.3 |
| 15.3 | 5.8 | 9.8 |
| 20.0 | 4.4 | 9.6 |
| 15.1 | 5.9 | 9.1 |
| 6.0 | 14.8 | 8.7 |
| 18.7 | 4.7 | 7.9 |
| 22.9 | 3.9 | 6.7 |
| 23.4 | 3.8 | 6.2 |
| 9.8 | 9.0 | 6.1 |
| 18.5 | 4.8 | 5.8 |
| 14.1 | 6.3 | 5.6 |
| 16.0 | 5.5 | 5.6 |
| 20.9 | 4.3 | 5.6 |
| 13.3 | 6.6 | 5.5 |
| 13.5 | 6.5 | 5.3 |
| 21.7 | 4.1 | 5.3 |
| 19.7 | 4.5 | 5.3 |

Example 2

Preparation of Supramolecular Complex Comprising Valsartan and AHU-377 Crystalline Form I To 0.5 mL of acetone was dissolved 104.1 mg of AHU-377 and 107.6 mg of valsartan and 29.4 mg of sodium hydroxide. Sonicated the solution and stirred it at room temperature until solids precipitated out. Added 2.5 mL acetone to it again and stirred at room temperature overnight. The solid was isolated and Form I was obtained, which was analyzed by XRPD, DSC and TGA. The XRPD data obtained in this example is listed in Table 2.

Figure 2:
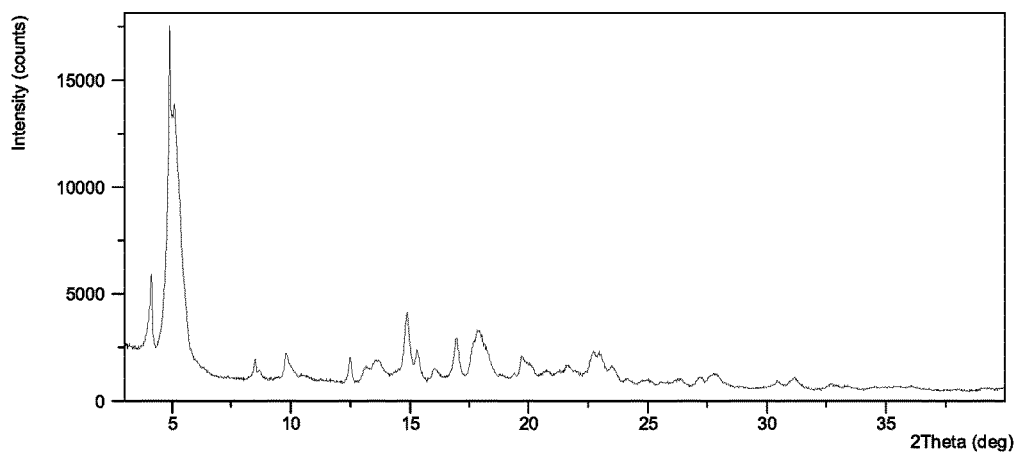
FIG. 2 shows an X-ray powder diffraction (XRPD) pattern of crystalline Form I obtained from example 2
Figure 4:
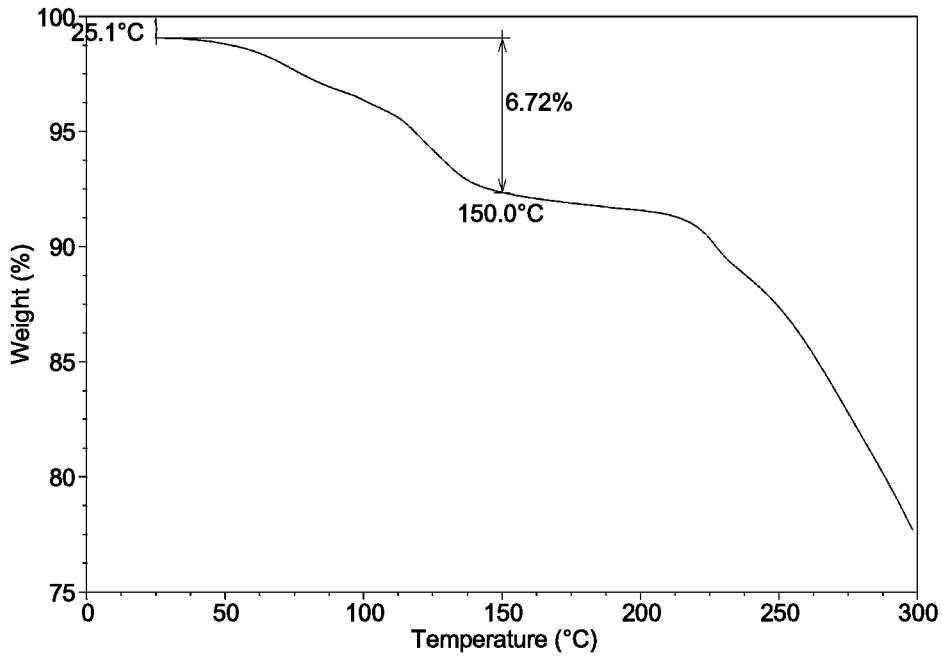
FIG. 4 shows a thermogravimetric analysis (TGA) thermogram of crystalline Form I obtained from example 2

The XRPD pattern, DSC thermogram, TGA thermogram of the complex obtained from this example are displayed in FIGS. 2-4, respectively.

TGA thermogram of the complex obtained from this example exhibits about 6.7% weight loss when heated up to 150° C.

TABLE 2

| Pos. [°2Th.] | d-spacing [Å] | Rel. Int. [%] |
|---|---|---|
| 4.2 | 21.1 | 25.2 |
| 5.0 | 17.9 | 100.0 |
| 5.1 | 17.2 | 77.2 |
| 5.4 | 16.5 | 50.6 |
| 8.6 | 10.3 | 4.6 |
| 9.9 | 9.0 | 7.2 |
| 10.7 | 8.3 | 1.3 |
| 12.6 | 7.1 | 5.7 |
| 13.2 | 6.7 | 3.4 |
| 13.6 | 6.5 | 5.8 |
| 14.9 | 5.9 | 20.4 |
| 15.4 | 5.8 | 8.6 |

TABLE 2-continued

| Pos. [°2Th.] | d-spacing [Å] | Rel. Int. [%] |
|---|---|---|
| 16.1 | 5.5 | 3.8 |
| 17.0 | 5.2 | 12.4 |
| 17.7 | 5.0 | 10.1 |
| 17.9 | 5.0 | 15.4 |
| 19.5 | 4.6 | 2.8 |
| 19.8 | 4.5 | 7.9 |
| 20.2 | 4.4 | 5.2 |
| 20.8 | 4.3 | 3.5 |
| 21.3 | 4.2 | 3.6 |
| 21.7 | 4.1 | 5.5 |
| 22.8 | 3.9 | 8.9 |
| 23.1 | 3.9 | 8.5 |
| 23.6 | 3.8 | 5.1 |

Example 3

Figure 5:
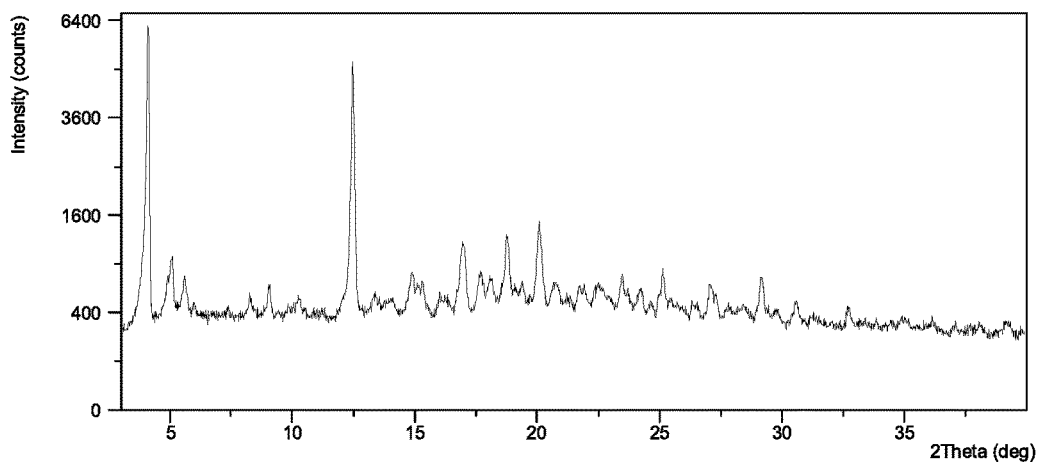
FIG. 5 shows an X-ray powder diffraction (XRPD) pattern of crystalline Form I obtained from example 3

Preparation of Supramolecular Complex Comprising Valsartan and AHU-377 Crystalline Form I To 1.0 mL of cumene was suspended 204.7 mg of Form II and stirred it at 50° C. for about 2 days. The solid was isolated and Form I was obtained, which was analyzed by XRPD and TGA. The XRPD pattern of the complex obtained from this example is displayed in FIG. 5.

TGA thermogram of the complex obtained from this example exhibits about 5.7% weight loss when heated up to 160° C.

Example 4

Preparation of Supramolecular Complex Comprising Valsartan and AHU-377 Crystalline Form I 1) Charged 6.0 g supramolecular complex comprising valsartan and AHU-377 crystalline Form II into a reactor, and charged 40 mL cumene to disperse the solids;
2) Stirred the slurry at 50° C. for 5 days, and cooled to RT;
3) Filtered the batch and dry the cake at 40° C. under vacuum to obtain Form I. (Yield: 5.9 g)

Figure 6:
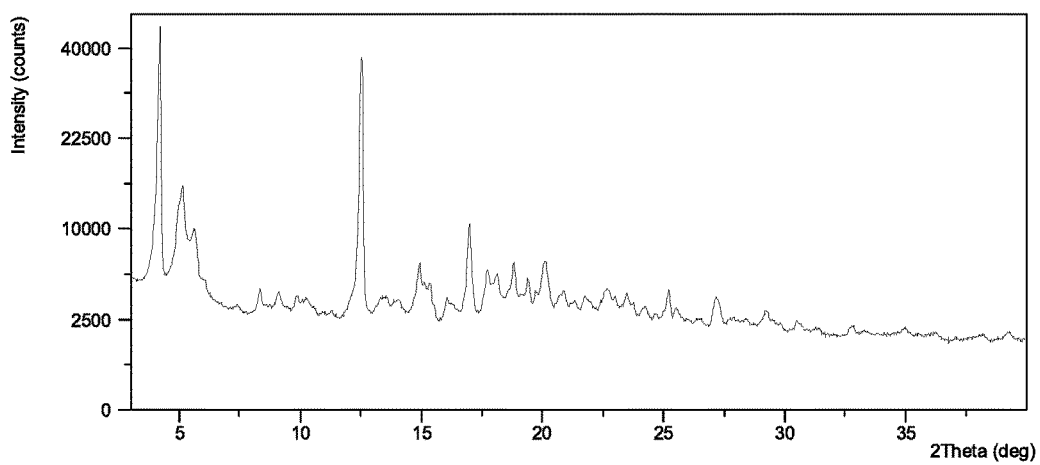
FIG. 6 shows an X-ray powder diffraction (XRPD) pattern of crystalline Form I obtained from example 4

The XRPD pattern of the complex obtained from this example is displayed in FIG. 6. TGA thermogram of the complex obtained from this example exhibited about 5.7% weight loss when heated up to 168° C. KF analysis exhibited water content of 6.4%.Example 5. Molar ratio determination of supramolecular complex comprising valsartan and AHU-377 crystalline Form I The molar ratio of supramolecular complex comprising valsartan and AHU-377 crystalline Form I was determined by high performance liquid chromatography (HPLC) analysis and ion chromatography analysis of a solution of AHU-377 supramolecular complex. The result displayed in Table 3 shows the molar ratio of AHU-377:valsartan:Na$^+$ in the supramolecular complex is 1:1:3.

TABLE 3

| Compound | AHU-377 supramolecular complex |
|---|---|
| Concentration of AHU-377 (mmol/L) | 1.89 |
| Concentration of valsartan (mmol/L) | 1.94 |
| Content of Na$^+$ (mmol/L) | 5.73 |
| Molar ratio (AHU-377:valsartan:Na$^+$) | 1:1:3 |

Example 6

Preparation of Supramolecular Complex Comprising Valsartan and AHU-377 Crystalline Form II To 11.0 mL of Methanol/Toluene (1/10; v/v) was dissolved 66.7 mg of trisodium [3-((1S,3R)-1-biphenyl-4-ylmethyl-3-ethoxycarbonyl-1-butylcarbamoyl) propionate-(S)-3'-methyl-2'-(pentanoyl{2"-(tetrazol-5-ylate)biphenyl-4'-ylmethyl}amino)butyrate] hemipentahydrate in a glass vial. Filtered the solution through a 0.45 μm filter and put to room temperature (RT) for slow evaporation with a pin-holed parafilm. The solid was isolated and supramolecular complex comprising valsartan and AHU-377 crystalline Form II was obtained, which was analyzed by XRPD and TGA. The XRPD pattern of the complex obtained from this example is displayed in FIG. 7. The XRPD data obtained in this example is listed in Table 4.

TGA thermogram of the complex obtained from this example exhibits about 6.3% weight loss when heated up to 150° C.

TABLE 4

| Pos. [°2Th.] | d-spacing [Å] | Rel. Int. [%] |
|---|---|---|
| 4.3 | 20.7 | 100.0 |
| 5.0 | 17.7 | 34.7 |
| 5.5 | 16.2 | 28.5 |
| 5.8 | 15.3 | 33.1 |
| 10.0 | 8.9 | 6.6 |
| 10.9 | 8.1 | 11.1 |
| 11.5 | 7.7 | 9.5 |
| 12.8 | 6.9 | 66.4 |
| 13.8 | 6.4 | 7.9 |
| 14.6 | 6.1 | 18.6 |
| 15.9 | 5.6 | 11.0 |
| 16.5 | 5.4 | 17.3 |
| 17.3 | 5.1 | 16.0 |
| 18.5 | 4.8 | 21.0 |
| 18.9 | 4.7 | 28.2 |
| 20.1 | 4.4 | 17.3 |
| 21.8 | 4.1 | 15.2 |
| 23.2 | 3.8 | 15.2 |

Example 7

Preparation of Supramolecular Complex Comprising Valsartan and AHU-377 Crystalline Form II To 0.2 mL of Methanol was added 9.9 mg of trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate. Heated the suspension at an 80° C. hot-stage plate for about 2 hours, filtered it and collected the hot supernatant. Equilibrated the hot supernatant at 80° C. for about 2 hours, then added 2.0 ml toluene to the hot supernatant drop-wise, stirred it at RT overnight. Then placed it for evaporation with cap open at RT. The solid was collected and crystalline Form II was obtained, which was analyzed by XRPD, DSC and TGA.

Figure 8:
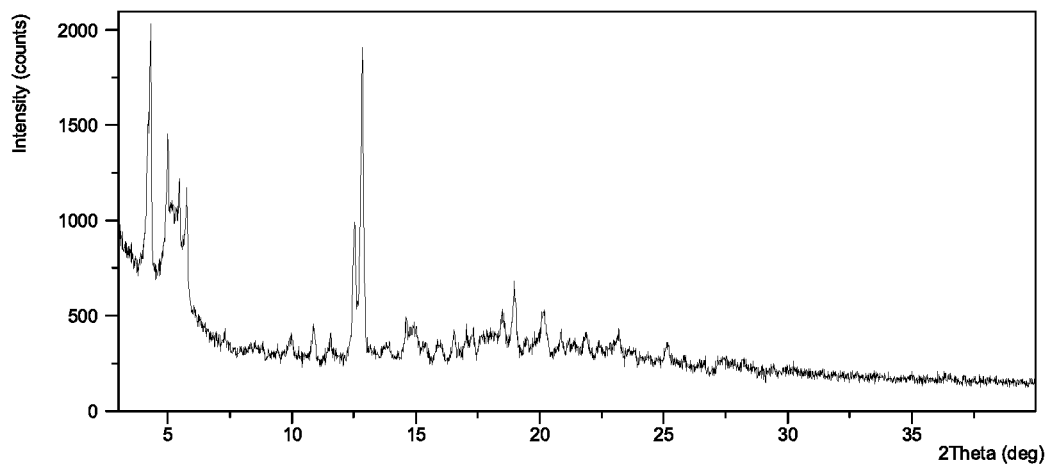
FIG. 8 shows an X-ray powder diffraction (XRPD) pattern of crystalline Form II obtained from example 7
Figure 10:
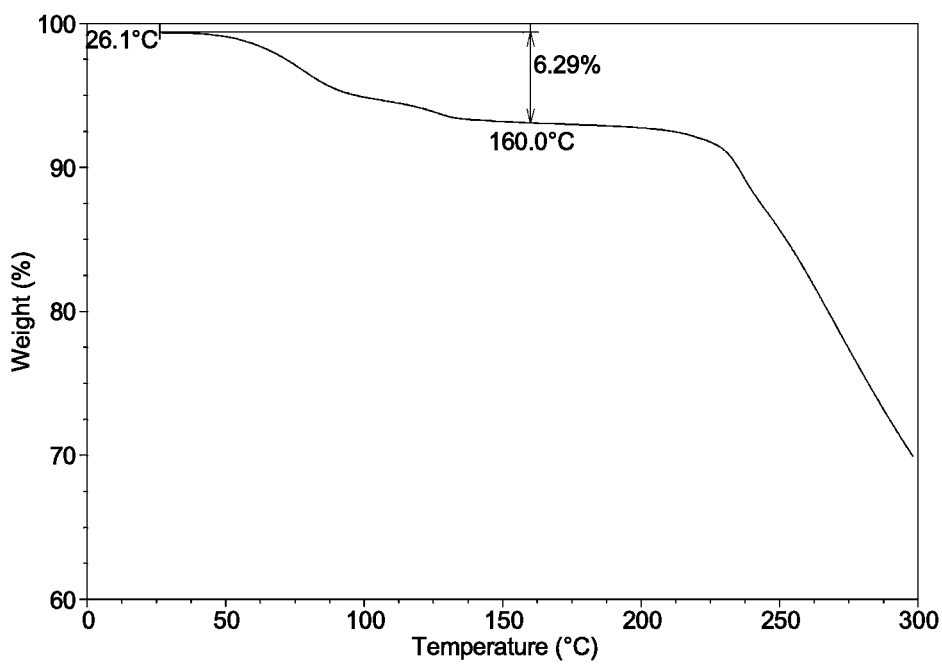
FIG. 10 shows a thermogravimetric analysis (TGA) thermogram of crystalline Form II obtained from example 7

The XRPD pattern, DSC thermogram, TGA thermogram of the complex obtained from this example are displayed in FIGS. 8-10, respectively. The XRPD data obtained for this example is listed in Table 5.

TGA thermogram of the complex obtained from this example exhibits about 6.3% weight loss when heated up to 160° C.

TABLE 5

| 2theta | d spacing | intensity % |
|---|---|---|
| 12.8 | 6.9 | 100.0 |
| 4.2 | 20.9 | 81.7 |
| 4.9 | 18.0 | 49.6 |
| 12.4 | 7.1 | 44.1 |
| 5.4 | 16.4 | 40.9 |
| 5.7 | 15.6 | 38.7 |
| 18.9 | 4.7 | 23.9 |
| 20.1 | 4.4 | 17.2 |
| 18.4 | 4.8 | 15.9 |
| 14.5 | 6.1 | 12.4 |
| 20.8 | 4.3 | 11.3 |
| 23.1 | 3.9 | 10.1 |
| 21.8 | 4.1 | 10.0 |
| 17.2 | 5.2 | 9.9 |
| 14.9 | 6.0 | 9.8 |
| 16.5 | 5.4 | 9.4 |
| 10.8 | 8.2 | 9.0 |
| 25.1 | 3.6 | 7.8 |
| 19.4 | 4.6 | 7.3 |
| 22.3 | 4.0 | 6.8 |
| 9.9 | 9.0 | 5.2 |

Example 8

Scale-Up Preparation of Supramolecular Complex Comprising Valsartan and AHU-377 Crystalline Form II 1) Charged 21.25 g AHU-377 and 23.20 g valsartan into a reactor, and charged 1 L toluene to disperse the solids;
2) Fed 45.56 g 13.49% (w/w) sodium hydroxide solution in methanol (6.15 g sodium hydroxide was dissolved into 50 ml methanol) for 1 hour;
3) Concentrated the solution at RT under vacuum;
4) Stopped concentrating and replenished 230 mL toluene to the initial total volume;
5) Dispersed 5.0 g Form II seeds in 50 mL toluene, and added the slurry into above solution to form a seed bed;
6) Mixed 3.33 mL pure water with 500 mL ethyl acetate, and fed the mixed solution into the seed bed for 1 hour;
7) Aged at RT for 3 hours;
8) Filtered the batch and dried the cake at 40° C. under vacuum. (Yield: 52.3 g)

Figure 11:
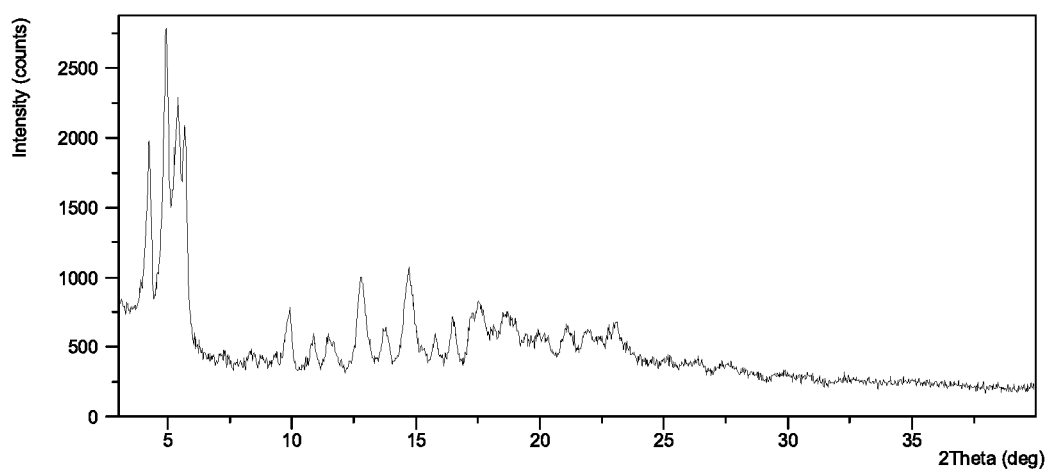
FIG. 11 shows an X-ray powder diffraction (XRPD) pattern of crystalline Form II obtained from example 8
Figure 12:
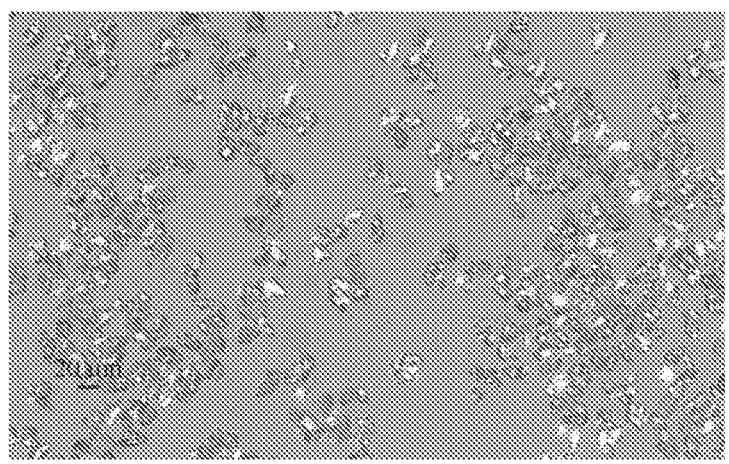
FIG. 12 shows polarized light microscopy (PLM) picture of crystalline Form II obtained from example 8

The XRPD pattern of the complex obtained from this example is displayed in FIG. 11. A PLM (polarized light microscopy) image of the sample is displayed in FIG. 12.

TGA thermogram of the complex obtained from this example exhibited about 6.7% weight loss when heated up to 150° C. KF result exhibited water content of 6.3%.

Example 9

Scale-Up Preparation of Supramolecular Complex Comprising Valsartan and AHU-377 Crystalline Form II 1) Charged 21.25 g AHU-377 and 23.20 g valsartan into a reactor, and charged 1 L toluene to disperse the solids;
2) Fed 45.57 g 13.49% (w/w) sodium hydroxide solution in methanol (6.15 g sodium hydroxide was dissolved into 50 mL methanol) for 1 hour;
3) Concentrated the solution at RT under vacuum;
4) Stopped concentrating and replenished 300 mL toluene to the initial total volume;
5) Dispersed 5.0 g Form II seeds in 50 mL toluene, and added the slurry into above solution to form a seed bed;
6) Mixed 3.33 mL pure water with 500 mL ethyl acetate, and fed the mixed solution into the seed bed for 1 hour;
7) Aged at RT for 3 hours;
8) Filtered the batch and dried the cake at 40° C. under vacuum. (Yield: 54.1 g)

Figure 13:
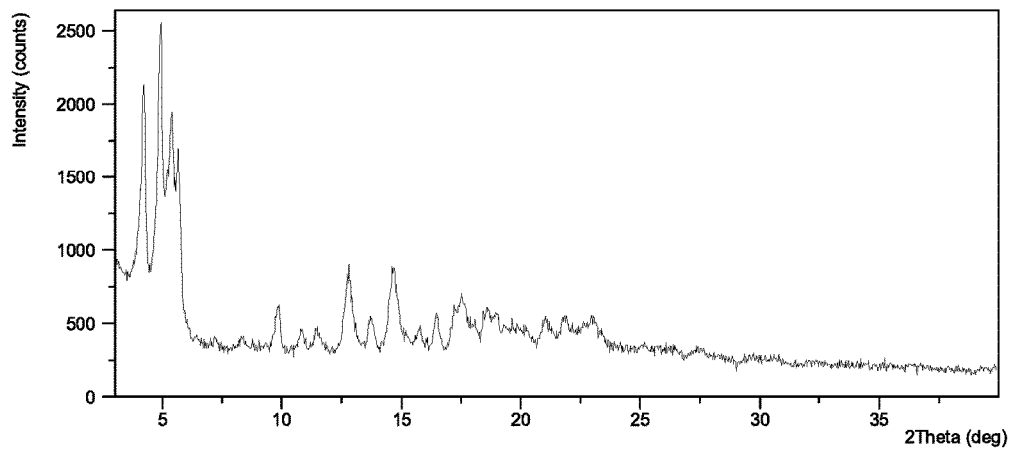
FIG. 13 shows an X-ray powder diffraction (XRPD) pattern of crystalline Form II obtained from example 9

The XRPD pattern of the complex obtained from this example is displayed in FIG. 13. TGA thermogram of the complex obtained from this example exhibits about 8.1% weight loss when heated up to 150° C.

Example 10

Scale-Up Preparation of Supramolecular Complex Comprising Valsartan and AHU-377 Crystalline Form II 1) Charged 2.16 g AHU-377 and 2.33 g valsartan into a reactor, and charged 50 mL toluene to disperse the solids;
2) Prepared sodium hydroxide solution in methanol (627 mg sodium hydroxide was dissolved into 4 ml methanol);
3) Added the sodium hydroxide solution to the reactor;
4) Filtered the solution and diluted it with 50 mL toluene;
5) Concentrated the solution at RT under vacuum-concentrated with $N_2$ protection;
6) Stopped concentrating and collected the solid after about 18 hours;
7) Dried the cake at 40° C. under vacuum (Yield: 4.70 g).

Figure 14:
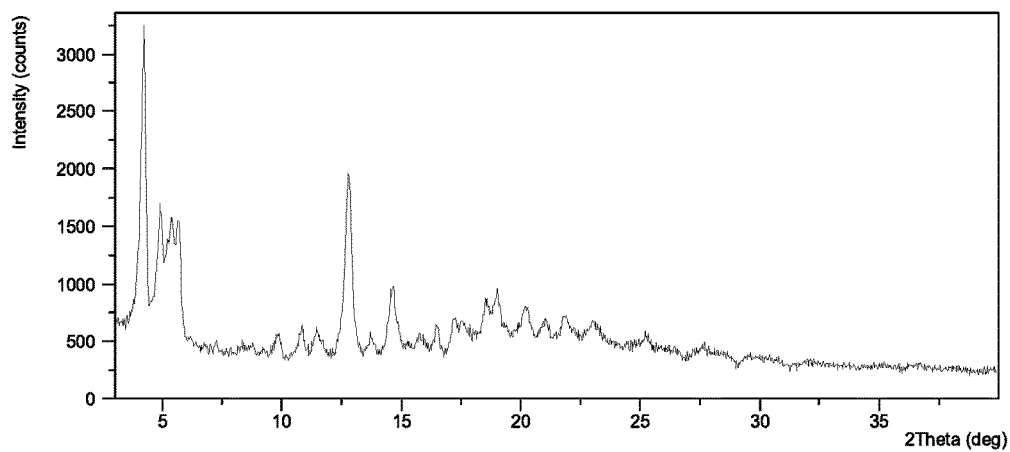
FIG. 14 shows an X-ray powder diffraction (XRPD) pattern of crystalline Form II obtained from example 10

The XRPD pattern of the complex obtained from this example is displayed in FIG. 14.

TGA thermogram of the complex obtained from this example exhibits about 7.13% weight loss when heated up to 146° C. Karl Fischer result exhibits that its water content is 7.18%.

Example 11

Molar Ratio Determination of Supramolecular Complex Comprising Valsartan and AHU-377 Crystalline Form II The molar ratio of supramolecular complex comprising valsartan and AHU-377 crystalline Form II was determined by high performance liquid chromatography (HPLC) analysis and ion chromatography analysis of a solution of supramolecular complex comprising valsartan and AHU-377 crystalline Form II. The result displayed in Table 6 shows the molar ratio of AHU-377: valsartan: Na in the supramolecular complex is 1:1:3.

TABLE 6

| Compound | AHU-377 supramolecular complex |
|---|---|
| Concentration of AHU-377 (mmol/L) | 2.00 |
| Concentration of valsartan (mmol/L) | 2.08 |
| Content of $Na^+$ (mmol/L) | 6.10 |
| Molar ratio (AHU-377:valsartan:$Na^+$) | 1:1:3 |

Example 12

Preparation of Supramolecular Complex Comprising Valsartan and AHU-377 Crystalline Form III 10 mg of supramolecular complex comprising valsartan and AHU-377 crystalline Form I was heated to 120° C. and Form III was obtained, which was characterized by XRPD.

Figure 17:
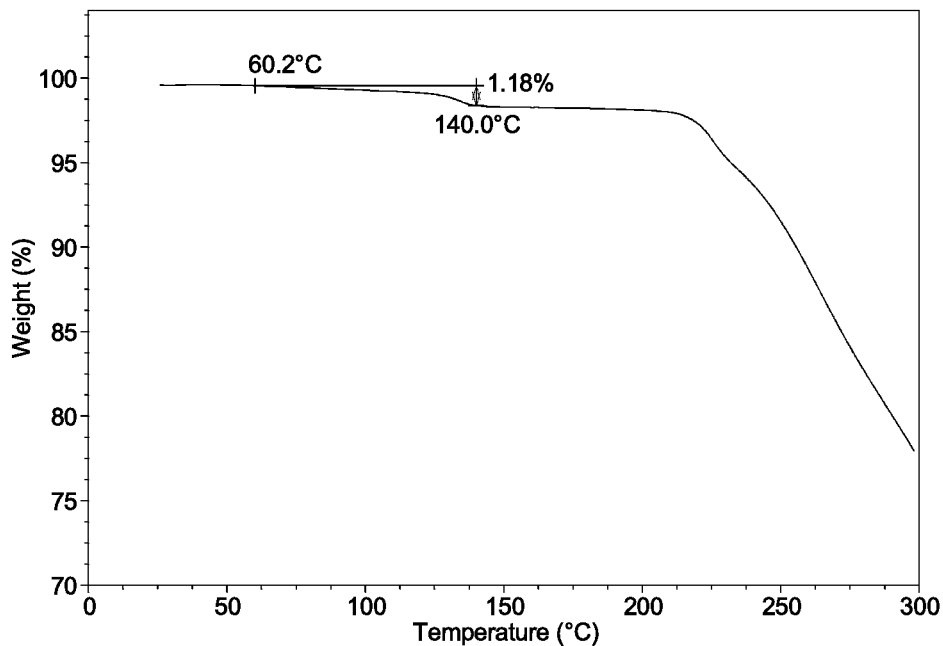
FIG. 17 shows a thermogravimetric analysis (TGA) thermogram of crystalline Form III obtained from example 12

The XRPD pattern, DSC thermogram, TGA thermogram of the complex obtained from this example are displayed in FIGS. 15-17, respectively. The XRPD data is listed in Table 7.

TGA thermogram of the complex obtained from this example exhibits about 1.2% weight loss when heated up to 140° C.

TABLE 7

| Pos. [°2Th.] | d-spacing [Å] | Rel. Int. [%] |
|---|---|---|
| 4.1 | 21.4 | 100.0 |
| 5.1 | 17.3 | 12.3 |
| 8.2 | 10.7 | 14.4 |
| 12.4 | 7.2 | 44.5 |
| 14.0 | 6.3 | 7.0 |
| 15.3 | 5.8 | 15.4 |
| 16.5 | 5.4 | 7.7 |
| 17.2 | 5.2 | 19.7 |
| 18.4 | 4.8 | 18.9 |
| 18.7 | 4.8 | 17.4 |
| 19.6 | 4.5 | 15.4 |
| 20.7 | 4.3 | 10.6 |
| 21.5 | 4.1 | 13.1 |
| 22.8 | 3.9 | 11.2 |
| 23.5 | 3.8 | 10.2 |
| 25.0 | 3.6 | 14.7 |
| 27.5 | 3.3 | 5.4 |
| 22.5 | 4.0 | 5.8 |
| 22.8 | 3.9 | 8.9 |
| 25.1 | 3.6 | 5.5 |

Example 13

DVS Comparison of Form I and Patent Form in U.S. Pat. No. 8,877,938B2

To obtain a water adsorption isotherm, a sample of polymorph Form I was placed on a microbalance in a sealed environmental chamber, and subsequently exposed to different humidity levels ranging from 0% RH or 20% RH to 60% RH, in 10% RH increments. At each humidity level, the polymorph was allowed to equilibrate until the sample experienced a dm/dt less than 0.02wt %. The equilibrium mass at each humidity level was recorded and, along with the dry sample weight, used to generate a plot of weight change versus relative humidity.

Figure 18:
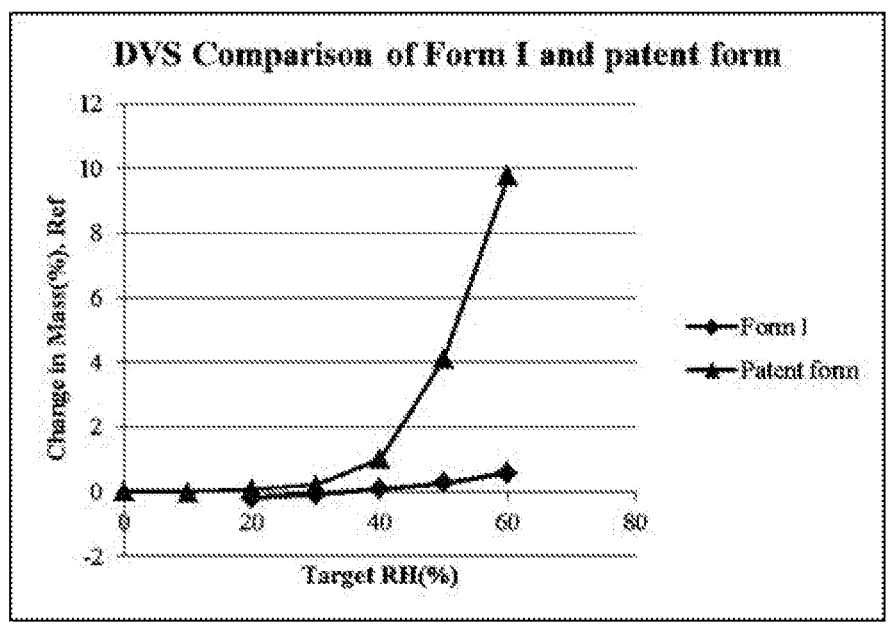
FIG. 18 shows DVS comparison of Form I and patent form in U.S. Pat. No. 8,877,938B2

FIG. 18 shows water adsorption isotherms (at 25° C.) for Form I and patent form reported in U.S. Pat. No. 8,877,938B2. Form I exhibits less moisture uptake when exposed to humidity levels ranging from 20% RH to 60% RH at 25° C. compared to patent form reported in U.S. Pat. No. 8,877,938B2.

Example 14

DVS Comparison of Form II and Patent Form in U.S. Pat. No. 8,877,938B2

To obtain a water adsorption isotherm, a sample of polymorph Form II was placed on a microbalance in a sealed environmental chamber, and subsequently exposed to different humidity levels ranging from 0% RH or 20% RH to 60% RH, in 10% RH increments. At each humidity level, the polymorph was allowed to equilibrate until the sample experienced a dm/dt less than 0.02wt %. The equilibrium mass at each humidity level was recorded and, along with the dry sample weight, used to generate a plot of weight change versus relative humidity.

Figure 19:
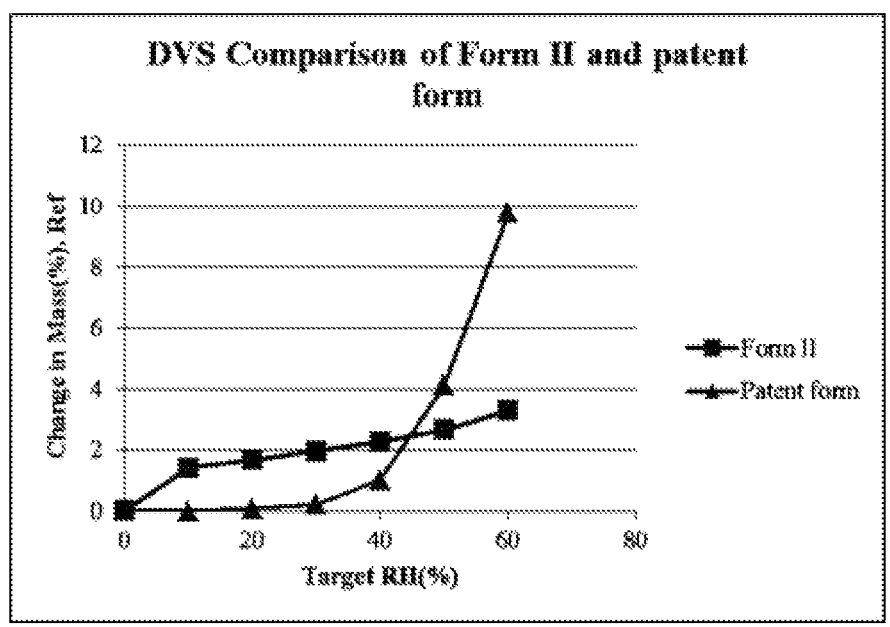
FIG. 19 shows DVS comparison of Form II and patent form in U.S. Pat. No. 8,877,938B2

FIG. 19 shows water adsorption isotherms (at 25° C.) for Form II and patent form reported in U.S. Pat. No. 8,877,938B2. Form II exhibits less moisture uptake when exposed to humidity levels ranging from 50% RH to 60% RH at 25° C. compared to patent form reported in U.S. Pat. No. 8,877,938B2.

Example 15

Evaluation of the Flowability of Form II and Patent Form in U.S. Pat. No. 8,877,938B2

The drug substances of Form II and patent form in U.S. Pat. No. 8,877,938B2 were evaluated for flowability following USP<1174> by compressibility index. The compressibility index was calculated with the following formula after testing of the bulk and tapped density of the powder. Results are listed in Table 9.

Compressibility Index(%)=(Tapped Density−Bulk Density)/Tapped Density*100%

TABLE 9

| Form | Bulk Density (g/ml) | Tapped Density (g/ml) | Compressibility Index (%) | Average (%) | Flowability |
|---|---|---|---|---|---|
| Patent form in U.S. Pat. No. 8,877,938B2 | 0.243 | 0.343 | 29 | 29 | Poor |
| | 0.245 | 0.346 | 29 | | |
| | 0.244 | 0.338 | 28 | | |
| | 0.240 | 0.347 | 31 | | |
| | 0.239 | 0.331 | 28 | | |
| Form II | 0.197 | 0.251 | 22 | 22 | Passable |
| | 0.229 | 0.297 | 23 | | |
| | 0.258 | 0.337 | 23 | | |

The compressibility index of Patent form in U.S. Pat. No. 8,877,938B2 is 29%, the flowability is poor, and the compressibility index of Form II is 22%, the flowability is passable. The results indicate that the flowabiltiy of Form II is better than that of patent form in U.S. Pat. No. 8,877,938B2.

Example 16

Crystal Form Stability of Drug Substance in Different Temperatures and Humidity Conditions 1. Form II Placed in Open Dish The drug substance of Form II was subjected to different relative humidity levels at 40° C. (±2° C.), samples were pulled out and evaluated for crystal form after a specified time period, the results are summarized in Table 10.

TABLE 10

| | RH | | |
|---|---|---|---|
| | 11% | 32% | 50% |
| Storage Period | 1 month | 1 month | 1 month |
| Form | II | II | II |

The drug substance of Form II was subjected to different temperatures at RH32%(±5%), samples were pulled out and evaluated for crystal form after a specified time period, the results are summarized in Table 11.

TABLE 11

| | Temperature | | | |
|---|---|---|---|---|
| | 30° C. | 40° C. | 50° C. | 60° C. |
| Storage Period | 1 month | 1 month | 2 weeks | 2 weeks |
| Form | II | II | II | II |

2. Form II Packed with Polyethylene (PE)

The drug substance of Form II was packed with PE to evaluate the stability. The result of accelerated stability (40° C., RH75%) indicates that the crystal form remained stable after one month.

3. Form II Stored in Glass Vial

The drug substance of Form II was stored in sealed glass vial under ambient conditions for 9 months. The result indicates that the crystal form remained stable after 9 months.

Example 17

Formulation of Supramolecular Complex Comprising Valsartan and AHU-377 Crystalline Form I The qualitative and quantitative formulation of immediate release AHU-377 and Valsartan/Tablets, 97 mg/103 mg, is presented in the table below. All components used are listed with weight, percent and function of each individual component.

TABLE 12

Composition of AHU-377 and Valsartan Tablets, 97 mg/103 mg

| Ingredient | mg/unit | % (w/w) | Function |
|---|---|---|---|
| Intra-granular Components | | | |
| Supramolecular complex comprising valsartan and AHU-377 crystalline Form I | 228.34*[1] | 57.09 | Bulk Active |
| Microcrystalline Cellulose | 89.66 | 22.41 | Filler |
| Low-substituted Hydroxypropyl Cellulose | 40.00 | 10.00 | Filler |
| Crospovidone | 12.00 | 3.00 | Disintegrant |
| Colloidal Silicon Dioxide | 2.00 | 0.50 | Glidant |
| Talc | 4.00 | 1.00 | Lubricant |
| Magnesium Stearate | 4.00 | 1.00 | Lubricant |
| Extra-granular Components | | | |
| Crospovidone | 12.00 | 3.00 | Disintegrant |
| Talc | 4.00 | 1.00 | Lubricant |
| Magnesium Stearate | 4.00 | 1.00 | Lubricant |
| Total | 400.0 | 100.0 | |

*[1]Equivalent to 97 mg of AHU-377 and 103 mg of Valsartan

The formulation was prepared according to the following procedure:

1) Mixed all of the intra-granular components, passed through screen with appropriate aperture dimension if necessary;
2) Compacted the powder mixture into flakes;
3) Milled the flakes, pass through 20 mesh;
4) Added extra-granular crospovidone and talc to the granulation in step 3 and mixed.
5) Added extra-granular magnesium stearate to the mixture in step 4 and mixed.
6) Compressed the final blend in step 5 into core tablets.

Example 18

Formulation of Supramolecular Complex Comprising Valsartan and AHU-377 Crystalline Form II The qualitative and quantitative formulation of immediate release AHU-377 and Valsartan Tablets, 97 mg/103 mg, is presented in Table 13. All components used in the manufacturing are listed with weight, percent and function of each individual component.

TABLE 13

Composition of Form II Tablets, 97 mg/103 mg

| Ingredient | mg/unit | % (w/w) | Function |
|---|---|---|---|
| Intra-granular Components | | | |
| supramolecular complex comprising valsartan and AHU-377 crystalline Form II | 230.50*[2] | 57.63 | Bulk Active |
| Microcrystalline Cellulose | 87.50 | 21.88 | Filler |
| Low-substituted Hydroxypropy Cellulose | 40.00 | 10.00 | Filler |
| Crospovidone | 12.00 | 3.00 | Disintegrant |
| Colloidal Silicon Dioxide | 2.00 | 0.50 | Glidant |
| Talc | 4.00 | 1.00 | Lubricant |
| Magnesium Stearate | 4.00 | 1.00 | Lubricant |
| Extra-granular Components | | | |
| Crospovidone | 12.00 | 3.00 | Disintegrant |
| Talc | 4.00 | 1.00 | Lubricant |
| Magnesium Stearate | 4.00 | 1.00 | Lubricant |
| Total | 400.0 | 100.0 | |

*[2]Equivalent to 97 mg of AHU-377 and 103 mg of Valsartan

The formulation was prepared according to the following procedure:

1) Mixed all of the intra-granular components, passed through screen with appropriate aperture dimension if necessary;
2) Compacted the powder mixture into flakes;

3) Milled the flakes, passed through 20 mesh;
4) Added extra-granular crospovidone and talc to the granulation in step 3 and mixed.
5) Added extra-granular magnesium stearate to the mixture in step4 and mixed.
6) Compressed the final blend in step 5 into core tablets.

The prepared core tablets were packaged with HDPE bottles and put on stability to evaluate the stability of the crystal form. The results of long-term stability (25° C.±2° C., RH60%±5%) indicate that the crystal form remained stable after three months, and the results of accelerated stability (40° C.±2° C., RH75%±5%) indicate that the crystal form remained stable after one month.

The foregoing examples and description of the preferred embodiments should be taken as illustrating, rather than as limiting, the present invention as defined by the claims. As will be readily appreciated, numerous variations and combinations of the features set forth above can be utilized without departing from the present invention as set forth in the claims.

What is claimed is:

1. A crystalline form of trisodium [3-((1S,3R)-1-biphenyl-4-ylmethyl-3-ethoxycarbonyl-1-butylcarbamoyl) propionate-(S)-3'-methyl-2'-(pentanoyl{2"-(tetrazol-5-ylate)biphenyl-4'-ylmethyl}amino)butyrate] hydrate, designated as Form I, characterized by an X-ray powder diffraction pattern comprising the following 2θ values measured using CuKα radiation: 5.1°±0.2°, 13.5°±0.2°, and 14.9°±0.2°.

2. The crystalline Form I of claim 1, wherein the X-ray powder diffraction pattern further comprises the following 2θ values measured using CuKα radiation: 4.1°±0.2°, 9.8°±0.2°, 12.5°±0.2°, and 16.9°±0.2°.

3. The crystalline Form I of claim 1, wherein the X-ray powder diffraction pattern further comprises the following 2θ values measured using CuKα radiation: 17.7°±0.2°, 18.0°±0.2°, and 19.7°±0.2°.

4. The crystalline Form I of claim 1, having an X-ray powder diffraction pattern substantially as depicted in FIG. 1.

5. A process of preparing the crystalline Form I according claim 1, comprising either of the steps 1) or 2) below:
1) dissolving valsartan, AHU-377 and sodium hydroxide in one or more alkyl ketones to form a solution; stirring the mixture at room temperature until crystalline Form I precipitates out; or
2) stirring crystalline Form II in one or more aromatic hydrocarbons at 40° C. to 80° C.

6. The process of claim 5, wherein said alkyl ketone is acetone, and said aromatic hydrocarbon is cumene.

7. A crystalline form of trisodium [3-((1S,3R)-1-biphenyl-4-ylmethyl-3-ethoxycarbonyl-1-butylcarbamoyl) propionate-N-3'-methyl-2'-(pentanoyl{2"-(tetrazol-5-ylate)biphenyl-4'-ylmethyl}amino)butyrate] hydrate, designated as Form II, characterized by an X-ray powder diffraction pattern comprising the following 2θ values measured using CuKα radiation: 4.3°±0.2°, 10.9°±0.2°, and 14.6°±0.2°.

8. The crystalline Form II of claim 7, wherein the X-ray powder diffraction pattern further comprises the following 2θ values measured using CuKα radiation: 5.0°±0.2°, 12.8°±0.2°, and 18.9°±0.2°.

9. The crystalline Form II of claim 7, wherein the X-ray powder diffraction pattern further comprises the following 2θ values measured using CuKα radiation: 5.5°±0.2°, 5.8°±0.2°, 18.5°±0.2°, and 20.1°±0.2°.

10. The crystalline Form II of claim 7, having an X-ray powder diffraction pattern substantially as depicted in FIG. 7.

11. A process of preparing the crystalline Form II according to claim 7, comprising either of the steps 1) or 2) below:
1) dissolving trisodium [3-((1S,3R)-1-biphenyl-4-ylmethyl-3-ethoxycarbonyl-1-butylcarbamoyl) propionate-(S)-3'-methyl-2'-(pentanoyl{2"-(tetrazol-5-ylate)biphenyl-4'-ylmethyl}amino)butyrate] hemipentahydrate in one or more alcohols to form a solution, adding one or more aromatic hydrocarbons to the solution, and stirring the mixture at room temperature until crystalline Form II precipitates out; or
2) dissolving trisodium [3-((1S,3R)-1-biphenyl-4-ylmethyl-3-ethoxycarbonyl-1-butylcarbamoyl) propionate-(S)-3'-methyl-2'-(pentanoyl{2"-(tetrazol-5-ylate) biphenyl-4'-ylmethyl}amino) butyrate] hemipentahydrate in one or two solvents selected from the group consisting of alcohols and aromatic hydrocarbons to form a solution; and evaporating the solvent(s) at room temperature until crystalline Form II precipitates out.

12. The process of claim 11, wherein said alcohol is methanol, and said aromatic hydrocarbon is toluene.

13. A crystalline form of trisodium [3-((1S,3R)-1-biphenyl-4-ylmethyl-3-ethoxycarbonyl-1-butylcarbamoyl) propionate-(S)-3'-methyl-2'-(pentanoyl{2"-(tetrazol-5-ylate)biphenyl-4'-ylmethyl}amino)butyrate] hydrate, designated as Form III, characterized by an X-ray powder diffraction pattern comprising the following 2θ values measured using CuKα radiation: 8.2°±0.2°, 17.2°±0.2°, and 21.5°±0.2°.

14. The crystalline Form III of claim 13, wherein the X-ray powder diffraction pattern further comprises the following 2θ values measured using CuKα radiation: 4.1°±0.2°, 12.4°±0.2°, 16.5°±0.2°, and 18.4°±0.2°.

15. The crystalline Form III of claim 13, wherein the X-ray powder diffraction pattern further comprises the following 2θ values measured using CuKα radiation: 19.6°±0.2°, 25.0°±0.2°, and 18.7°±0.2°.

16. The crystalline Form III of claim 13, having an X-ray powder diffraction pattern substantially as depicted in FIG. 15.

17. A process for preparation of crystalline Form III according to claim 13, comprising heating Form I to 100° C. to 140° C.

18. A pharmaceutical composition comprising a crystalline form of the supramolecular complex selected from the group consisting of crystalline Form I, crystalline Form II, crystalline Form III, and combinations thereof, and a pharmaceutically acceptable carrier.

19. The crystalline Form I of claim 1, having an X-ray powder diffraction pattern substantially as depicted in FIG. 2.

* * * * *